(12) United States Patent
Brown

(10) Patent No.: US 10,016,487 B2
(45) Date of Patent: Jul. 10, 2018

(54) PROCESS FOR PURIFYING LACTOFERRIN FROM MILK AND PRODUCTS THEREOF

(71) Applicant: Murray Gouldburn Co-operative Co. Ltd., Southbank (AU)

(72) Inventor: Andrew Brown, Point Cook (AU)

(73) Assignee: Murray Goulburn Co-Operative Co. Ltd., Southbank (AU)

( * ) Notice: Subject to any disclaimer, the term of this patent is extended or adjusted under 35 U.S.C. 154(b) by 0 days.

(21) Appl. No.: 14/434,324

(22) PCT Filed: Oct. 8, 2013

(86) PCT No.: PCT/AU2013/001152
§ 371 (c)(1),
(2) Date: Apr. 8, 2015

(87) PCT Pub. No.: WO2014/056025
PCT Pub. Date: Apr. 17, 2014

(65) Prior Publication Data
US 2015/0315264 A1 Nov. 5, 2015

(30) Foreign Application Priority Data

Oct. 8, 2012 (AU) ................................ 2012904391
Apr. 12, 2013 (AU) ................................ 2013204858

(51) Int. Cl.
| C07K 1/34 | (2006.01) |
| A61K 38/40 | (2006.01) |
| C07K 14/79 | (2006.01) |
| A61K 38/48 | (2006.01) |
| A23J 1/20 | (2006.01) |

(52) U.S. Cl.
CPC ................ *A61K 38/40* (2013.01); *A23J 1/20* (2013.01); *A61K 38/482* (2013.01); *C07K 14/79* (2013.01); *A23V 2002/00* (2013.01); *C12Y 304/21* (2013.01)

(58) Field of Classification Search
CPC ..... C07K 14/79; A61K 38/482; C12Y 304/21
USPC .................................................... 424/94.64
See application file for complete search history.

(56) References Cited

U.S. PATENT DOCUMENTS

| 5,194,591 | A * | 3/1993 | Bottomley ........... A23C 9/1425 |
| | | | 210/767 |
| 5,221,734 | A | 6/1993 | Burk et al. |
| 5,756,680 | A * | 5/1998 | Ahmed ................ A21D 2/263 |
| | | | 426/271 |
| 2003/0059512 | A1 | 3/2003 | Kopf et al. |
| 2005/0208638 | A1* | 9/2005 | Wu ....................... A23C 21/00 |
| | | | 435/192 |
| 2006/0040025 | A1 | 2/2006 | Souppe |
| 2006/0178311 | A1* | 8/2006 | Wilde ....................... C07K 7/06 |
| | | | 514/4.7 |
| 2010/0047428 | A1 | 2/2010 | Lejars et al. |
| 2010/0136172 | A1* | 6/2010 | Brown .................... A23C 9/146 |
| | | | 426/63 |
| 2011/0123514 | A1* | 5/2011 | McDonagh ............... A23J 1/20 |
| | | | 424/94.6 |
| 2013/0195990 | A1* | 8/2013 | Rowney .................. A23C 21/06 |
| | | | 424/535 |

FOREIGN PATENT DOCUMENTS

| CN | 102348387 A | 2/2012 | |
| EP | 0 556 083 A1 | 8/1993 | |
| EP | 0 869 134 A1 | 10/1998 | |
| EP | 2 599 493 A1 | 6/2013 | |
| GB | 2179947 A * | 3/1987 | ........... A23C 9/1465 |
| JP | H05-202098 A | 8/1993 | |
| WO | 93/13676 A1 | 7/1993 | |
| WO | 03/073866 A1 | 9/2003 | |
| WO | 2006/029518 A1 | 3/2006 | |
| WO | 2010/112988 A1 | 10/2010 | |
| WO | 2012/015037 | 2/2012 | |

OTHER PUBLICATIONS

Maubois "Ultrafiltration of whey" Journal of the Society of Dairy Technology, vol. 33, No. 2, Apr. 1980 pp. 55-58.*
Odendaal "Purification of the Alpha Toxin of Clostridium Perfringens Type A by Ultrafiltration and Gel Chromatography" Onderstepoon J. Vet. Res., 54, 39-43 (1987).*
International Search Repoert for PCT/AU2013/001152.
Supplementary European Search Report mailed Mar. 9, 2016 in corresponding EP 13844731.3.
Lu et al., "Isolation of lactoferrin from bovine colostrum by ultrafiltration coupled with strong cation exchange chromatography on aproduction scale", Journal of Membrane Science, vol. 297, pp. 152-161 (2007).
Third Part Observation issued in corresponding EP 13844731.3 dated Sep. 13, 2017.
Japanese Office Action dated Aug. 28, 2017 in corresponding Japanese Patent Application No. 2015-534883.
M. Murata et al., "Identification of milk proteins enhancing the antimicrobial activity of lactoferrin and lactoferricin", J. Dairy Sci., 96:4891-4898 (2013).

(Continued)

*Primary Examiner* — Louise Wang Zhiying Humphrey
*Assistant Examiner* — Stephen A Perkins
(74) *Attorney, Agent, or Firm* — Mintz Levin Cohn Ferris Glovsky and Popeo, P.C.; Peter F. Corless

(57) ABSTRACT

The invention provides a process for purifying lactoferrin from milk, the process comprising subjecting the milk to filtration to separate it into a retentate fraction comprising lactoferrin and a permeate fraction comprising growth factors and/or RNAses, wherein prior to and/or during filtration the milk is subjected to salt treatment such that growth factors and/or RNAses flow into the permeate. The invention also provides lactoferrin obtained from the process of the invention and uses thereof.

3 Claims, 6 Drawing Sheets

(56) References Cited

OTHER PUBLICATIONS

H. Ueno et al., "Functional characteristics of Iron-lactoferrin complex and its application to food products", Milk Science, 61(2), pp. 105-113 (2012).

* cited by examiner

PROCESS FOR PURIFYING LACTOFERRIN FROM MILK AND PRODUCTS THEREOF

CROSS-REFERENCE TO RELATED APPLICATONS

This application is a National Phase application filed under 35 USC 371 of PCT International Application No. PCT/AU2013/001152 with an International Filing Date of Oct. 8, 2013, which claims under 35 USC § 119(a) the benefit of Australian Application No. 2012904391, filed Oct. 8, 2012 and Australian Application No. 2013204858, filed Apr. 12, 2013, the entire contents of which are incorporated herein by reference.

FIELD

This invention relates generally to processes for purifying proteins of interest from milk.

BACKGROUND

Milk from domestic animals has been used as a source of protein and other products for the food and pharmaceutical industries for many years, and a variety of techniques are known for isolating these products. Milk is a colloidal suspension composed primarily of fats, lactose and proteins in water. Among ruminants and laboratory animals, milk contains an average of 30 to 140 grams of protein per liter, or about 4-17% by weight, depending on the species. The bulk of these proteins are caseins, which are complexed with calcium and phosphate in supramolecular structures known as micelles. The other major class of milk proteins is whey proteins, predominantly comprised of beta-lactoglobulin and alpha-lactalbumin, but also including lactoferrin, immunoglobulins, and serum albumin.

Milk proteins usually are isolated by a combination of processes including membrane filtration techniques as well as ion exchange adsorption procedures.

Lactoferrin is an 80 kD iron-binding glycoprotein found naturally in biological fluids such as saliva, bile, bronchial mucus, gastrointestinal fluids, cervico-vaginal mucus, seminal fluid, and milk. The richest source of lactoferrin is mammalian milk and colostrum. The concentration of lactoferrin in bovine skimmed milk is usually small, typically between 80-200 mg/ml depending on factors including the pasteurisation and other pre-treatment history of the skimmed milk. After precipitation of the casein present in milk, the concentration of lactoferrin in bovine whey is typically 10-100 mg/ml depending on the physical and chemical pre-treatment of the whey.

Lactoferrin has multiple postulated biological roles, including regulation of iron metabolism, immune function, and embryonic development. Lactoferrin has anti-microbial activity against a range of pathogens including Gram positive and Gram negative bacteria and fungi, including yeasts. The anti-microbial effect of lactoferrin is based on its capability of binding iron, which is essential for the growth of the pathogens. Lactoferrin also inhibits the replication of several viruses and increases the susceptibility of some bacteria to antibiotics and lysozyme by binding to the lipid A component of lipopolysaccharides on bacterial membranes.

It is an aim of a preferred embodiment of the present invention to provide an improved method for purifying lactoferrin from milk, particularly bovine milk, to improve purity.

All references, including any patents or patent applications, cited in this specification are hereby incorporated by reference. It will be clearly understood that, although a number of prior art publications are referred to herein, this reference does not constitute an admission that any of these documents forms part of the common general knowledge in the art.

SUMMARY

A first aspect provides a process for purifying lactoferrin from milk, the process comprising subjecting the milk to filtration to separate it into a retentate fraction comprising lactoferrin and a permeate fraction comprising growth factors and/or RNAses, wherein prior to and/or during filtration the milk is subjected to salt treatment such that growth factors and/or RNAses flow into the permeate.

When purifying lactoferrin from milk using membrane filtration with a 30 kD or 50 kD cut off the inventors found that the lactoferrin retentate was contaminated with growth factors and RNAses. As these growth factors and RNAses have a molecular weight of less than 30 kD they should have passed through the membrane and into the permeate. Growth factors and RNAses should not be present as an impurity in the retentate lactoferrin fraction. Accordingly the discovery of growth factors and RNAses in the retentate was surprising. With the aim of further purifying the lactoferrin fraction the inventors found that the addition of a large amount of salt to the milk prior to filtration removed the growth factors and RNAses from the retentate, thus further purifying the lactoferrin. Under salt conditions the growth factors and RNAses were found in the permeate.

Without wishing to be bound by theory, the inventors propose that under normal conditions the RNAses and growth factors in milk aggregate or otherwise form a mass that is larger than their individual molecular weights. It is proposed that the salt treatment causes the RNAses and growth factors to disaggregate or disassociate.

Accordingly in an alternative form, the process of the first aspect provides a process for purifying lactoferrin from milk the process comprising subjecting the milk to filtration to separate it into a retentate fraction comprising lactoferrin and a permeate fraction comprising growth factors and/or RNAses, wherein prior to and/or during filtration the milk is subjected to salt treatment capable of disaggregating or disassociating any mass of RNAses or growth factors so that growth factors and/or RNAses flow into the permeate.

Without wishing to be bound by theory, the inventors alternatively propose that under conditions of low ionic strength, protein aggregates may become associated with the membrane, thereby forming a layer with a smaller apparent pore size to that of the membrane, which prevents RNAses and growth factors in milk passing through the membrane. It is proposed that the salt treatment prevents formation of or removes the protein layer, allowing any RNAses and growth factors to pass through the membrane into the permeate.

Accordingly in an alternative form, the process of the first aspect provides a process for purifying lactoferrin from milk the process comprising subjecting the milk to membrane filtration to separate the milk into a retentate fraction comprising lactoferrin and a permeate fraction comprising growth factors and/or RNAses, wherein prior to and/or during filtration the milk is subjected to salt treatment capable of separating any RNAses or growth factors from the membrane such that growth factors and/or RNAses flow into the permeate.

A second aspect provides lactoferrin obtained from the process of the first aspect.

In one embodiment the lactoferrin of the second aspect is subjected to further purification.

A third aspect provides the use of lactoferrin of the second aspect for as an anti-cancer, anti-viral, anti-microbial or anti-inflammatory agent, for treating proliferative disorders such including cancer, particularly those involving solid tumours, for treating malignant neoplasms and hyperproliferative diseases, for treating bone disorders by promoting osteogenesis, for treating viral or microbial infections, for corneal wound treatment, to boost immunity, to treat B-cell non-Hodgkin lymphoma, to treat septic shock, to improve gut health by improving bifidus numbers while decreasing *E. coli, streptococcus* and *clostridium*, to treat IBD, for promoting immunity and resistance to disease, to manage systemic inflammation, to prevent organ transplant rejection and graft versus host disease, to improve maternal and fetal health, to improve neuronal health and infant gut development, to reduce the likelihood of pregnancy-associated complications such as pre-eclampsia, preterm labour, gestational diabetes, miscarriage, intrauterine fetal death, premature delivery, low birth weight, placental abruption and intrauterine growth restriction, particularly in a woman with hypoferremia or iron deficiency anemia, for treating iron deficiency and anemia, particularly in pregnant women, for the prevention of neonatal sepsis in premature newborns, for wound healing, to promote biofilm formation, to treat oral infections including periodontitis, for treating diabetic ulcers, in the treatment of cystic fibrosis, in the reduction of pain, to treat proteinalbinuria, to promote growth of skin cells, as a radioprotective agent, in the treatment of urinary tract infections, in the treatment of degenerative joint diseases, in the treatment of diabetes, in the treatment of respiratory disorders, in the reduction of circulating cholesterol, vascular inflammation, atherosclerosis and cardiovascular disease and in all other uses of lactoferrin known to persons skilled in the art.

In an alternative form, the third aspect provides lactoferrin obtained from the process of the first aspect for use as proposed in the third aspect or for use in the manufacture of a medicament for use as proposed in the third aspect.

DETAILED DESCRIPTION

Figure 1:
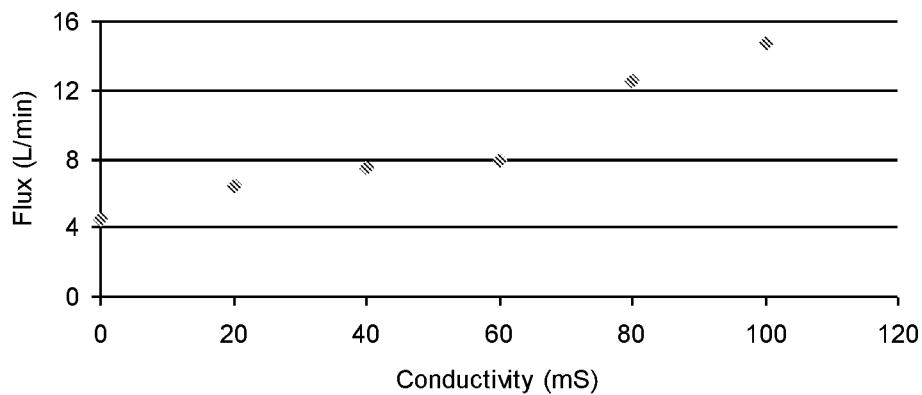
FIG. 1 shows permeate flux across a 50 kDa membrane increases as conductivity increases.

The present invention provides improved methods for purifying lactoferrin from milk or enriching milk for lactoferrin.

The inventors have recognised the need for a process which allows the preparation of enriched lactoferrin in an efficient manner.

The terms "purified" or "enriched", as used herein in relation to lactoferrin means that the lactoferrin protein: total protein ratio present in the retentate is increased relative to the ratio present in the milk before the filtration step. For the fraction to be considered enriched or purified, it should have a lactoferrin content of at least 1, 2, 3, 4, 5, 6, 7, 8, 9, 10, 11, 12, 13, 14, 15, 16, 17, 18, 19, 20, 22, 25, 27, 28, or 30, 40, 50, 60, 70, 80, 90, 95, 96, 97, 98, 98, or 99% w/w higher than in milk before the filtration step.

The process of the first aspect seeks to increase the purity of the lactoferrin retentate to up to 100% pure.

As used herein, the term "fraction" refers to a partially purified portion of milk.

Use of the term "efficient" is taken to mean an inexpensive and quick process when compared to methods which are currently employed to enrich for proteins.

Reference herein to milk includes whole milk, skim milk, buttermilk, whey (such as acid or cheese/renneted whey) or a whey derivative (such as whey protein concentrate or whey protein isolate flow through), and colostrum. It also includes milk fractions, for example fractions that have been subjected to purification steps such as cation exchange chromatography. Such fractions include milk basic protein and enriched lactoferrin fractions.

It will be apparent to those skilled in the art that the milk may be obtained from any lactating animal, e.g. ruminants such as cows, sheep, buffalos, goats, and deer, non-ruminants including primates such as a human, and monogastrics such as pigs. It is preferred that skim milk which is derived from whole cow's milk is used in the process of the present invention.

The filtration used in the process of the first aspect comprises membrane filtration. In one embodiment the membrane has a size cut off of 30 kD, 35 kD, 40 kD, 45 kD, 50 kD.

The filtration may involve ultrafiltration or diafiltration or both.

The salt treatment used in the process of the first aspect involves adding sufficient salt so that the ionic strength of the milk is at least 0.2 M (1.1%) NaCl or equivalent. In one embodiment the ionic strength is maintained at least this level for a period required to obtain the required increase in lactoferrin purity. This period may be at least 10 minutes, 15 minutes, 20 minutes, 30 minutes, 45 minutes, 1 hour, 2 hours, 3 hours, 4 hours, 5 hours, 6 hours, 7 hours, 8 hours, 9 hours, 10 hours, 11 hours, 12 hours or more depending on the milk feed material and the increase in purity desired.

In an alternative the salt treatment used in the method of the first aspect involves adding sufficient salt so that the conductivity of the milk is at least 20 mS/mm. In one embodiment the conductivity is maintained at at least this level during the entire filtration step.

Generally the milk will have an ionic strength of substantially less than 0.2M NaCl or equivalent or less than 20 mS/mm conductivity and hence the salt treatment involves the addition of salt to increase the ionic strength or conductivity of the milk to the desired level. However in some circumstances, for example when the milk is a fraction that has been subjected to cation exchange, the milk will have an ionic strength that may be at least 0.2 M NaCl or equivalent or the conductivity will be 20 mS/mm or more. Generally fractions from cation exchange are subjected to treatment to remove salt (e.g. diafiltration with water). However according to the process of the first aspect the salt treatment is such to maintain the ionic strength of the milk at at least 0.2 M (1.1%) NaCl or equivalent during the filtration step or to maintain the conductivity of the milk at at least 20 mS/mm during the filtration step.

As used herein "conductivity" is the ability of a material to conduct electric current. Conductivity is generally measured using a conductivity meter for example a HACH SENSION 5. Persons skilled in the art would be aware of suitable alternative means to measure conductivity. There is a generally linear relationship between sodium ion concentration and conductivity.

The salt used in the salt treatment is not limited and alternatives to NaCl would be known to the person skilled in the art. For example any soluble, non-toxic buffer can be used such as the soluble sodium, potassium, calcium, magnesium or lithium salts of chloride, citrate, phosphate, acetate, sulphate, bicarbonate, hydroxide, imidazole, or maleate. Synthetic zwitterion buffers such as Trizma, HEPES or tricine may also be used.

To allow separation of the RNAses and growth factors from lactoferrin the ionic strength of the milk must be at least 0.2 M (1.1%) NaCl or equivalent or more prior to the filtration step. In one embodiment the ionic strength of the milk is increased by adding 1.1%, salt, 1.5% salt, 2% salt, 2.5% salt, 3% salt, 3.5% salt, 4% salt, 4.5% salt, 5% salt, 5.5% salt, 6% salt or more. In another embodiment the ionic strength of the milk is increased to 0.2M, 0.22M, 0.24M, 0.26M, 0.28M, 0.30M, 0.32M, 0.34M, 0.36M, 0.38M, 0.40M, 0.42M, 0.44M, 0.46M, 0.48M, 0.50M, 0.6M, 0.7M, 0.8M, 0.9M, 1.0M NaCl or equivalent or more. In another embodiment, the conductivity is 20 mS/mm, 30 mS/mm, 40 mS/mm, 50 mS/mm, 60 mS/mm, 70 mS/mm, 80 mS/mm, 90 mS/mm, 100 mS/mm, and 110 mS/mm, 120 mS/mm or more.

In a preferred embodiment the salt treatment involves the addition of 0.2-0.5M NaCl or KCl to the milk prior to the filtration step.

In one embodiment the salt treatment is carried out at 4-10 degrees.

In one embodiment the salt treatment is carried out at 10-30 degrees.

In one embodiment the salt treatment is carried out at 30-50 degrees.

In one embodiment the salt treatment is carried out at 50-70 degrees.

In one embodiment the salt treatment is carried out at less than 20 degrees.

In another embodiment the salt treatment is carried out at 50 degrees or higher as at temperatures in excess of 50 degrees coliform formation is reduced. However as lactoferrin denatures at roughly 70 degrees performing the salt treatment at 60 degrees or above may result in decreased yield.

In one embodiment the filtration step is carried out at 4-10 degrees.

In one embodiment the filtration step is carried out at 10-30 degrees.

In one embodiment the filtration step is carried out at 30-50 degrees.

In one embodiment the filtration step is carried out at 50-70 degrees.

In one embodiment the salt treatment is carried out at atmospheric pressure.

In one embodiment the filtration step is carried out at a transmembrane pressure less than 2.5 Bar per membrane, more likely less than 2.0 Bar, more likely again less than 1.5 Bar but ideally 1.0-1.4 Bar, although a pressure of 0.0-1.0 Bar could also work acceptably but have a lower transmembrane flux.

"Treating" or "treatment" refers to both therapeutic treatment and prophylactic or preventative measures, wherein the aim is to prevent, ameliorate, reduce or slow down (lessen) or improve a condition, disease or disorder.

"Treating" or "treatment" as used herein covers any treatment of, or prevention of a condition in a vertebrate, a mammal, particularly a human.

"Preventing", "prevention", "preventative" or "prophylactic" refers to keeping from occurring, or to hinder, defend from, or protect from the occurrence of a condition, disease, disorder, or phenotype, including an abnormality or symptom. A subject in need of prevention may be prone to develop the condition.

The term "ameliorate" or "amelioration" refers to a decrease, reduction or elimination of a condition, disease, disorder, or phenotype, including an abnormality or symptom. A subject in need of treatment may already have the condition, or may be prone to have the condition or may be in whom the condition is to be prevented.

The term "maintain" as used herein refers to sustaining a condition at pre-treatment levels.

The lactoferrin of the second aspect may be provided as a pharmaceutical, veterinary or nutraceutical composition or as a food.

A pharmaceutical composition is one which is suitable for administration to humans. A veterinary composition is one that is suitable for administration to animals. Generally such compositions will contain purified lactoferrin or at the very least all components of the composition will be verifiable.

The pharmaceutical or veterinary composition may comprise one or more carriers and optionally other therapeutic agents. Each carrier, diluent, adjuvant and/or excipient may be "acceptable".

By "acceptable" is meant a material which is not biologically or otherwise undesirable, i.e., the material may be administered to an individual along with the selected active agent without causing any undesirable biological effects or interacting in a deleterious manner with any of the other components of the pharmaceutical or veterinary composition in which it is contained. Similarly, an "acceptable" salt or ester of a novel compound as provided herein is a salt or ester which is not biologically or otherwise undesirable.

As used herein, a "carrier" is an acceptable solvent, suspending agent or vehicle for delivering the agent to the subject. The carrier may be liquid or solid and is selected with the planned manner of administration in mind. Each carrier must be "acceptable" in the sense of being not biologically or otherwise undesirable i.e. the carrier may be administered to a subject along with the agent without causing any or a substantial adverse reaction.

The pharmaceutical or veterinary composition may be administered orally, topically, or parenterally in formulations containing conventional non-toxic acceptable carriers, adjuvants, and vehicles.

The term parenteral as used herein includes intravenous, intraarterial, intraperitoneal, intramuscular, subcutaneous, subconjunctival, intracavity, transdermal and subcutaneous injection, aerosol for administration to lungs or nasal cavity or administration by infusion by, for example, osmotic pump.

The pharmaceutical or veterinary composition may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar.

Suitable flavouring agents include peppermint oil, oil of wintergreen, cherry, orange or raspberry flavouring. Suitable preservatives include sodium benzoate, vitamin E, alphatocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate. The tablets may contain the agent in admixture with non-toxic pharmaceutically acceptable excipients which are suitable for the manufacture of tablets.

These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, growth factors and inert gases and the like.

The pharmaceutical or veterinary composition may also contain other active compounds providing supplemental, additional, or enhanced therapeutic functions. The pharmaceutical or veterinary composition may also be included in a container, pack, or dispenser together with instructions for administration.

The pharmaceutical or veterinary composition can be administered in one dose, or at intervals such as once daily, once weekly, and once monthly.

Dosage schedules can be adjusted depending on the half life of the active agent, or the severity of the subject's condition.

Generally, the pharmaceutical or veterinary composition is administered as a bolus dose, to maximize the circulating levels of active agent for the greatest length of time after the dose. Continuous infusion may also be used after the bolus dose.

The lactoferrin of the second aspect may be provided in a nutraceutical composition or food.

The term "nutraceutical" as used herein refers to an edible product isolated or purified from food, in this case from a milk product, which is demonstrated to have a physiological benefit or to provide protection or attenuation of an acute or chronic disease or injury when orally administered. The nutraceutical may thus be presented in the form of a dietary preparation or supplement, either alone or admixed with edible foods or drinks.

The nutraceutical composition may be in the form of a soluble powder, a liquid or a ready-to-drink formulation. Alternatively, the nutritional composition may be in solid form as a food; for example in the form of a ready-to-eat bar or breakfast cereal. Various flavours, fibres, sweeteners, and other additives may also be present.

The nutraceutical preferably has acceptable sensory properties (such as acceptable smell, taste and palatability), and may further comprise vitamins and/or minerals selected from at least one of vitamins A, B1, B2, B3, B5, B6, B11, B12, biotin, C, D, E, H and K and calcium, magnesium, potassium, zinc and iron.

The nutraceutical composition may be produced as is conventional; for example, the composition may be prepared by blending together the protein and other additives. If used, an emulsifier may be included in the blend. Additional vitamins and minerals may be added at this point but are usually added later to avoid thermal degradation.

If it is desired to produce a powdered nutraceutical composition, the protein may be admixed with additional components in powdered form. The powder should have a moisture content of less than about 5% by weight. Water, preferably water which has been subjected to reverse osmosis, may then be mixed in to form a liquid mixture.

If the nutraceutical composition is to be provided in a ready to consume liquid form, it may be heated in order to reduce the bacterial load. If it is desired to produce a liquid nutraceutical composition, the liquid mixture is preferably aseptically filled into suitable containers. Aseptic filling of the containers may be carried out using techniques commonly available in the art. Suitable apparatus for carrying out aseptic filling of this nature is commercially available.

Preferably the nutraceutical composition also comprises one or more pharmaceutically acceptable carriers, diluents or excipients. Nutraceutical compositions may comprise buffers such as neutral buffered saline, phosphate buffered saline and the like; carbohydrates such as glucose, mannose, sucrose or dextrans; mannitol; proteins; polypeptides or amino acids such as glycine; antioxidants; chelating agents such as EDTA; adjuvants and preservatives.

The nutraceutical may be an infant formula, particularly a humanised milk formula for administration to infants.

When provided as a food the lactoferrin of the second aspect can take the form of a food supplement, a nutritional formulation, a sports nutrition supplement or an infant formula. In one embodiment the food is animal feed.

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

It must also be noted that, as used in the subject specification, the singular forms "a", "an" and "the" include plural aspects unless the context clearly dictates otherwise.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

EXAMPLES

The invention is now further described in detail by reference to the following examples. The examples are provided for purposes of illustration only, and are not intended to be limiting unless otherwise specified. Thus, the invention encompasses any and all variations which become evident as a result of the teaching provided herein.

Example 1: Ultrafiltration of Lactoferrin to Remove Small Molecules and Increase Lactoferrin Purity An APV pilot scale ultrafiltration plant was fitted with a single 6 inch 50 kDa membrane (Synder) and then stabilised so that the baseline pressure was 3.2-3.4 Bar and the transmembrane pressure 1.2-1.4 Bar. Lactoferrin solution (2 mg/mL) was split into six lots of 2 L. In six experiments that were identical, except for the conductivity (0, 20, 40, 60, 80 or 100 mS/mm), 2 L lactoferrin solution was added to the ultrafiltration feed tank, topped to 170 L with water and adjusted to the nominated conductivity by adding sodium chloride solution. Retentate was recycled to the feed tank and permeate was collected. The permeate removed was replaced with diafiltration solution of the same conductivity. Purity was assessed by cation exchange HPLC.

Figure 2:
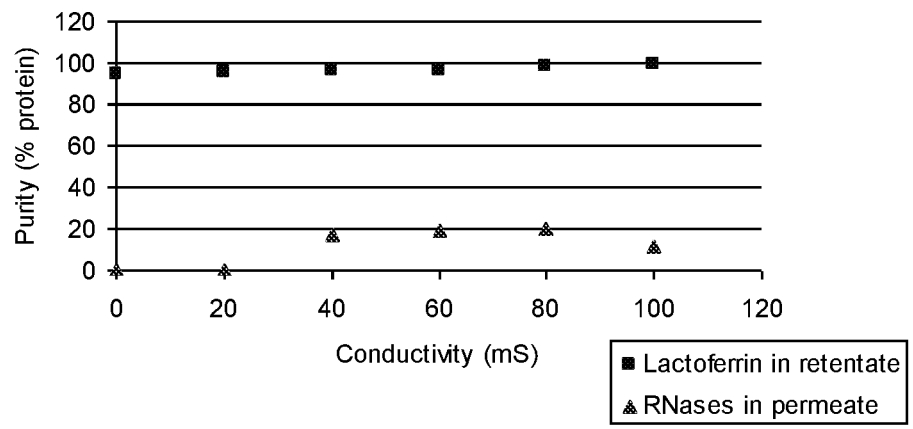
FIG. 2 shows that ultrafiltration (UF) in the presence of increasing sodium chloride concentration increases the purity of retained lactoferrin by increasing the permeation of low molecular weight contaminants (RNAses used as an example).
Figure 3:
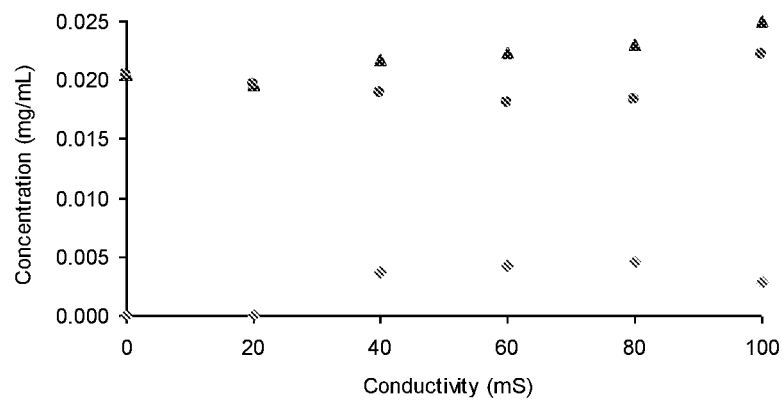
FIG. 3 shows the concentration of lactoferrin (●), low molecular weight proteins (RNAses used as an example, ♦) and protein (▲) in the permeate from a 50 kDa UF membrane.

It was found that increasing salt concentration increased the permeate flux (FIG. 1). Lactoferrin purity was increased from 95% (0 mS/mm) to 98.4% (100 mS/mm) (FIG. 2). The concentrations of the components permeating is shown in FIG. 3, which shows that at 100 mS/mm the amount of lactoferrin and total protein increases. Both the increase in purity and the increase in flux suggest that extra sodium chloride improves the process and that a conductivity of at least 40 mS/mm is necessary for the process to occur optimally. The lactoferrin solution eluted from chromatographic plants and collected in UF4 is intended to be 96 mS/mm, so the optimum increase in lactoferrin purity occurring in the region between 80 mS/mm and 100 mS/mm is compatible with the existing process without further processing.

Example 2: Salt Disaggregates Lactoferrin

Lactoferrin (95% lactoferrin as percentage of protein) was dissolved in water at 10 mg/mL. A HPLC was fitted with a SUPERDEX 200 10/300 GL column (GE Healthcare) and equilibrated with Buffer A (Tris.HCl (pH 7, 1 g/L)) at a flow of 0.5 mL/min. Buffer B is Tris.HCl (1 g/L) containing 1M sodium chloride (pH 7) and the sample injected was 100 µL. The amount of Buffer B was 0% between 0 min to 50 min, increased to 100% buffer B between 50 min and 90 min and then increased to 16% Buffer B from 90 min to 150 min. During each of the subsequent runs, the salt between 0 min to 50 min and 90 min to 150 min increased by 16% B.

Figure 4:
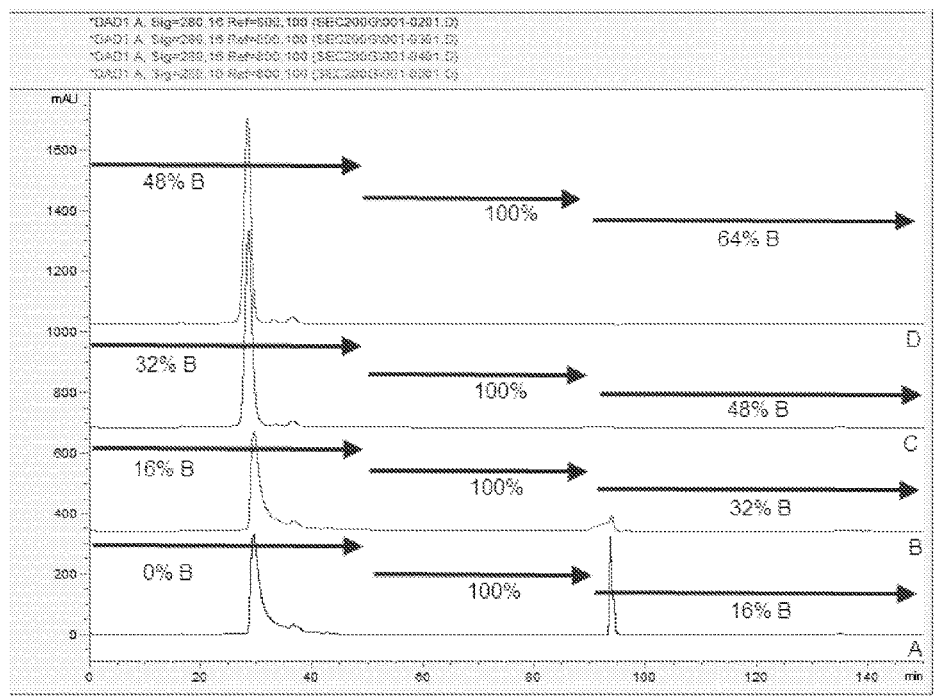
FIGS. 4 A,B,C and D show size exclusion high performance liquid chromatography (HPLC) analysis of lactoferrin in increasing concentrations of sodium chloride, showing that increasing concentrations disaggregate large particles. The sodium chloride concentration within the first 50 minutes is the important difference between the four chromatographs: A, 0 M NaCl; B, 0.16 M NaCl; C, 0.32 M NaCl and D, 0.48 M NaCl.

As shown in FIG. 4, the lactoferrin elutes in a single major peak at approximately 28 min and is followed by several smaller peaks, which include lactoferrin fragments and non-lactoferrin proteins. Chromatograph D shows, which contained 0.48M NaCl, is an example of a typical lactoferrin profile. Chromatograph A, which contained no NaCl, showed the presence of a smaller lactoferrin peak and a larger peak at 94 min. The peak at 94 min is lactoferrin that was insoluble until the higher salt commencing at 50 min dissociated the aggregated lactoferrin and allowed it to move through the resin bed contained in the column.

The results shown in FIG. 4 confirm that salt dissociates the proteins present in the 95% lactoferrin powder, although the proteins dissociated are not necessarily lactoferrin, and leads to individual proteins that will pass through a 50 kDa membrane. The results indicate that greater than 0.32M NaCl is required for the dissociation effect to occur.

This experiment has been repeated with liquid samples and similar results were observed.

Example 3: Ultrafiltration of Lactoferrin to Remove Small Molecules and Increase Lactoferrin Purity Six VIVACELL 250 units (Sartorius) were fitted with 50 kDa membranes. Each was filled to the 250 mL line with 1 mg/mL lactoferrin solution, but each had a different sodium chloride concentration (0, 1.5, 3, 4, 5 or 6% NaCl). The cells were pressurised to 3 Bar. Samples of retentate and permeate were collected and analysed by cation exchange HPLC.

Figure 5:
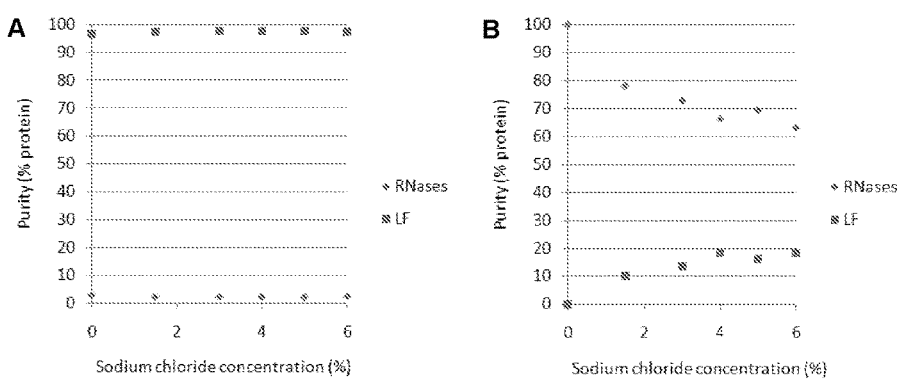
FIGS. 5A and B show ultrafiltration of a lactoferrin solution through a 50 kDa membrane held in a VIVACELL apparatus, in the presence of sodium chloride (0, 1.5, 3, 4, 5, or 6% NaCl), showing that in the presence of sodium chloride, the 50 kDa membrane selectively allows the transmission of RNAses and other growth factors. A: permeate samples; B, retentate samples.
Figure 6:
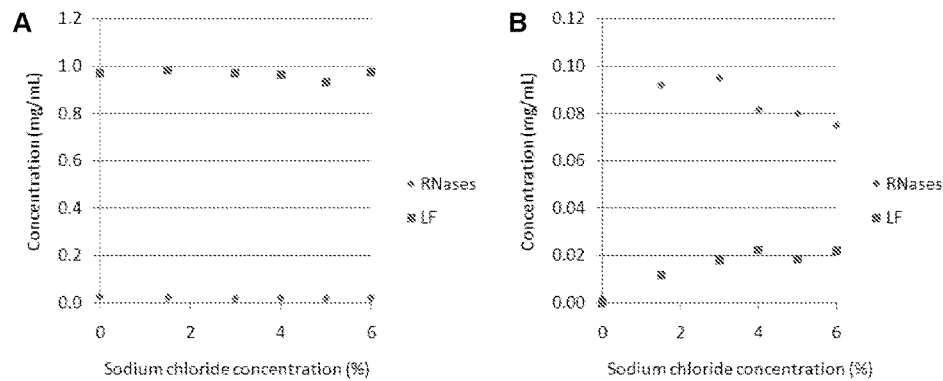
FIGS. 6A and 6B shows ultrafiltration of a lactoferrin solution through a 50 kDa membrane held in a VIVACELL apparatus, in the presence of sodium chloride (0, 1.5, 3, 4, 5, or 6% NaCl), showing that in the presence of sodium chloride, the 50 kDa membrane selectively allows the transmission of RNAses and other growth factors. A: permeate samples; B, retentate samples.

It was found that increasing salt concentration increased the transmission of growth factors (RNAses used as a representative) and increased the purity of the lactoferrin in the retentate (FIGS. 5 and 6).

Example 4: Ultrafiltration of Lactoferrin to Remove Small Molecules and Increase Lactoferrin Purity An ultrafiltration plant was fitted with a single 6 inch 50 kDa membranes (Synder) and then stabilised so that the baseline pressure was 3.2-3.4 Bar and the transmembrane pressure 1.2-1.4 Bar. Lactoferrin solution (2 mg/mL) was split into six lots of 2 L. In six experiments that were identical, except for the conductivity (0, 20, 40 or 60 mS/mm), 2 L lactoferrin solution was added to the UF feed tank, topped to 170 L with water and adjusted to the nominated conductivity by adding sodium chloride solution. Retentate was recycled to the feed tank and permeate was collected. The permeate removed was replaced with diafiltration solution of the same conductivity. Purity was assessed by cation exchange HPLC.

Figure 7:
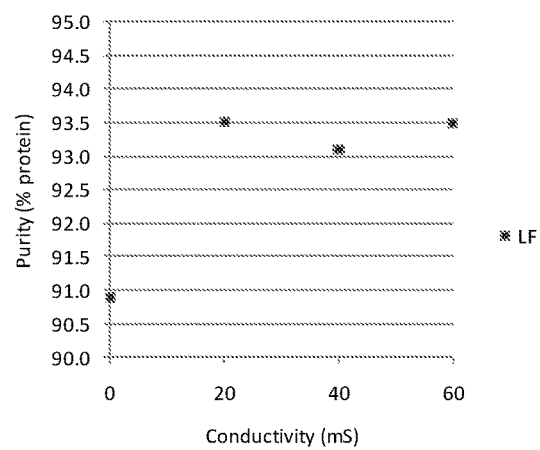
FIG. 7 shows ultrafiltration in the presence of increasing conductivity increases the purity of retained lactoferrin.
Figure 8:
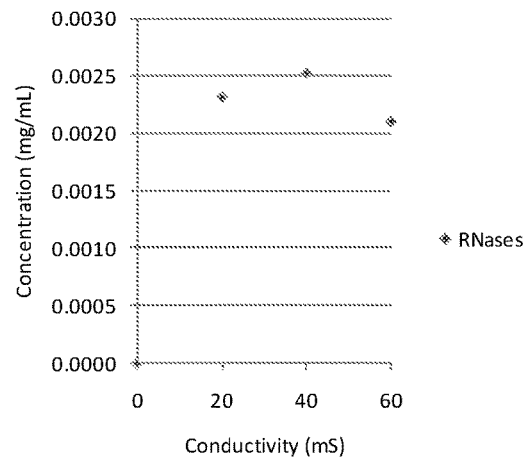
FIG. 8 shows that increased lactoferrin purity is due to the increased transmission of contaminating growth factors, such as the RNAses. Growth factor transmission increases quickly between 0 mS/mm and 20 mS/mm.

Lactoferrin purity was increased from 90.9% (0 mS/mm) to 93.5% (60 mS/mm) (FIG. 7), which represents a 2.5% increase in purity. The increase in lactoferrin purity was achieved by the selective removal of growth factors (RNAses used as an example, FIG. 8).

Example 5: Using Secondary Cation Exchange Chromatography with or without Ultrafiltration to Improve Increase Lactoferrin Purity Lactoferrin powder (40 g, 95.2% lactoferrin) was dissolved in water (200 mL) with a Stomacher. A sample was collected and analysed by cation exchange HPLC. The lactoferrin solution was applied to a column (50 mmD×1000 mmL) filled with SP FAST FLOW resin (GE Healthcare). The bound lactoferrin was eluted from the resin with a linear gradient of 3 L, ranging from 0% to 5.8% (1 M) sodium chloride. The main lactoferrin peak was collected and analysed by cation exchange HPLC.

A small amount of the main lactoferrin peak (5 mL) was placed in a centrifuge-driven 50 kDa UF device (Sartorius Stedim), diluted to three times the initial volume (15 mL) with water, centrifuged (8,000 g×20 min) until 1.5 mL of lactoferrin remained and finally analysed by cation exchange HPLC.

Figure 9:
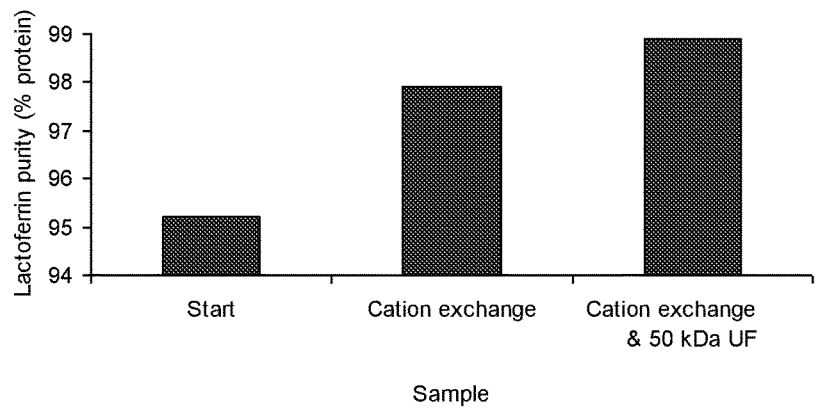
FIG. 9 shows lactoferrin purity in the lactoferrin starting material, main cation exchange chromatography peak and the material further purified by ultrafiltration using a 50 kDa membrane. Target lactoferrin purity is 98%.

The combination of cation exchange chromatography and 50 kDa UF obtained a purity of 98.9%, which exceeded the required purity of 98% protein, whereas chromatography alone (97.8%) did not (FIG. 9). Cation exchange chromatography increased the purity of the lactoferrin by 2.7% and the subsequent 50 kDa UF step increased the purity by a further 0.9%. Promisingly, 50 kDa UF increased the purity, even in a material that was already extremely pure and it appears that 50 kDa UF by itself would be worth trialling.

Example 6: Initial Experiment to Determine if Ultrafiltration of Lactoferrin can Increase Lactoferrin Purity Sufficiently Lactoferrin powder (1 kg, purity 96.3% protein) was dissolved in 100 L water. The lactoferrin solution was placed in an APV UF plant fitted with a single Synder 6.3" 50 kDa membrane (BX-5XB-6338). The combined volume of the lactoferrin solution and the water present in the UF plant was 180 L and the conductivity was 58 mS/mm due to added sodium chloride. Permeate (100 L) was removed in 10 min. Water (100 L) and salt were added to obtain a conductivity of 121 mS/mm. Permeate (100 L) was removed in 10 min. The conductivity of the lactoferrin retentate was then reduced to 1300 µS by water diafiltration (400 L permeate). The lactoferrin retentate was then freeze-dried (48 h, 1 mBar, 40° C.). Liquid samples were analysed by cation exchange HPLC and powder samples were analysed by cation exchange HPLC by an external laboratory (samples analysed in the powder form should be considered more accurate).

Figure 10:
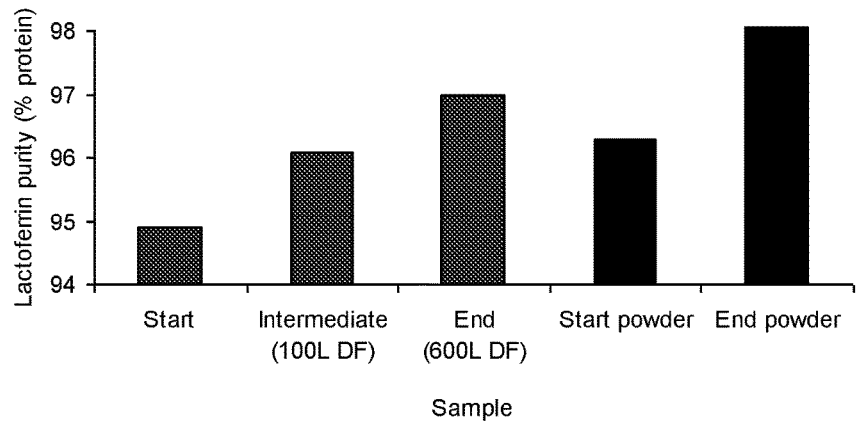
FIG. 10 illustrates the increase in lactoferrin purity during processing with 50 kDa membranes. Samples analysed by cation HPLC in the liquid form are indicated in grey and samples analysed by cation exchange HPLC in the powder form are indicated in black.

The purity of lactoferrin can be increased by approximately 2% (protein basis) when sufficient diafiltration has occurred in an UF plant fitted with 50 kDa membranes. The final purity result was 98.1% (protein basis) (FIG. 10), which shows that the process may be viable and further development is warranted.

Figure 11:
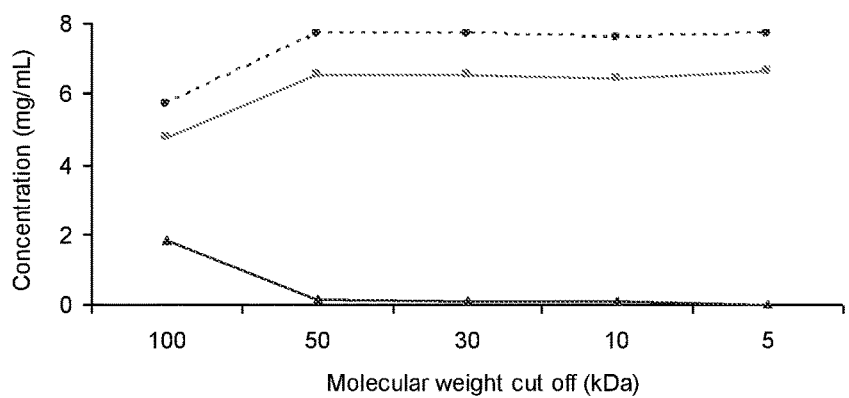
FIG. 11 illustrates that when lactoferrin solutions containing sodium chloride are processed by ultrafiltration, increasing membrane molecular weight cut off allows an increasing amount of protein to pass into the permeate (□▲□) and improves the retention of protein (···●···) and lactoferrin (□■□). Results have been obtained by testing separating 2 mg/mL lactoferrin solution containing 6% sodium chloride with Sartorius Stedium VIVACELL 250 UF membranes of the indicated porosities.
Figure 12:
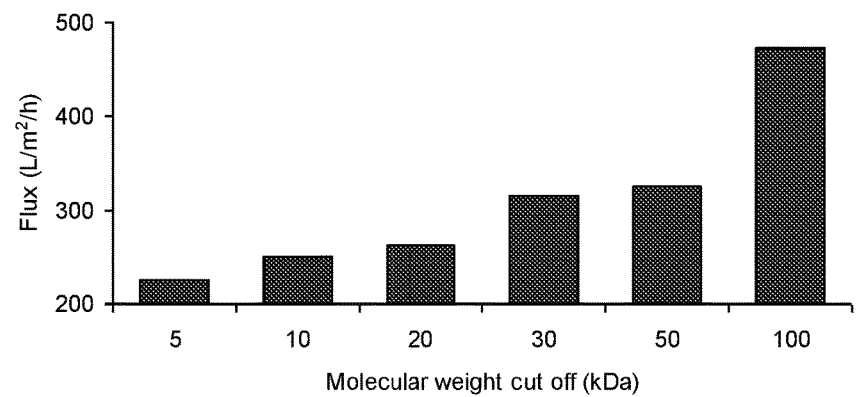
FIG. 12 illustrates that flux of membranes increases with molecular weight cut off (data obtain from Synder Filtration, water processed at 25° C. and 3.4 Bar), but is not appreciably different between 30 kDa and 50 kDa.
Figure 13:
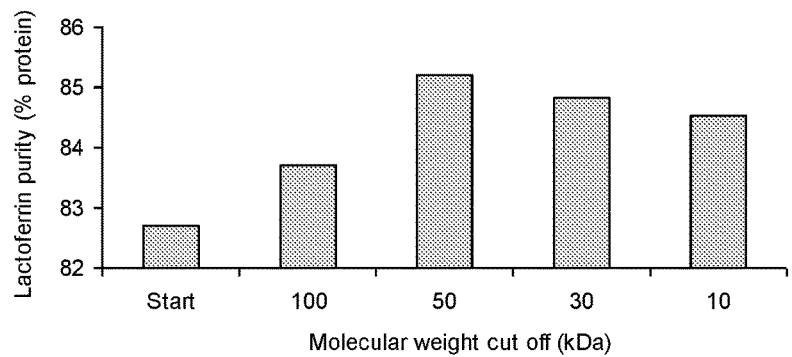
FIG. 13 illustrates that when lactoferrin solutions containing sodium chloride are processed by ultrafiltration, increasing membrane molecular weight cut off increases the purity until the membrane porosity is 50 kDa. Results have been obtained by testing separating 2 mg/mL lactoferrin solution containing 6% sodium chloride with Sartorius Stedium VIVACELL 250 UF membranes of the indicated porosities.

Example 7: Effect of Membrane Molecular Weight Cut Off on Membrane Performance Membrane molecular weight cut off (MWCO) is the most important influence on membrane performance. As the pore size of the membrane increases, the membrane allows the passage of larger proteins (FIG. 11) and the flux increases (FIG. 12). Membranes have the capacity to separate components in mixtures, but only if one or some components are smaller than the membrane MWCO and one or some components are larger than the membrane MWCO. In general, a difference in molecular weight of at least two orders of magnitude are required for ideal separations (i.e. 28 Da water and 58 Da sodium chloride can be almost completely separated from 78 kDa lactoferrin), but some separation is possible where such a significant differential in size is not present. If the aim is to increase the purity of lactoferrin solution, the 50 kDa membrane appears to be the best option available (FIG. 13).

Example 8: Ultrafiltration Membranes

UF4

Type: Spiral wound polyethersulfone (PES) MWCO: 30 kDa
Brand: Synder Model: MK2B-6338
The ultrafiltration plant known as UF4 was used to:
1. concentrate lactoferrin eluted from the cation exchange column, and
2. recycle the lactoferrin elution salt back to the 6% salt tank for reuse in the chromatographic process.
Justification of Process within the Broader Lactoferrin Manufacturing Process:
sodium chloride (2,000 kg per batch) is a significant cost ($1,200 per batch) in the lactoferrin manufacture process and the ability to recycle sodium chloride dramatically reduces the cost of production.

environmental damage is reduced by recycling sodium chloride. After tertiary treatment at Leongatha to remove organic solids, sodium chloride-containing effluent is disposed of by means of an ocean outfall and all steps must be taken to reduce the amount of waste generated. The salt recycling process reduces the amount of salt required by 80%, meaning that the amount of sodium chloride released into the environment is reduced by 8,000 kg per batch (two-thirds due to UF4).

Justification of Membrane Type:

spiral membranes are a comparatively cheap way of obtaining a large area of membrane, which allows high fluxes in a plant with a small foot print.

PES is an inherently hydrophilic membrane that wets out quickly and completely resulting in fast filtration with superior flow rates and high throughputs. PES membrane is also extremely low protein binding minimizing the likelihood of target protein binding, which means high yields, stable transmembrane fluxes and consistent apparent membrane porosities.

Justification of MWCO:

30 kDa membranes successfully retain the harvested lactoferrin (protein transmission through the membrane is 0.6% of the protein present), which increases purity by allowing key contaminants, especially RNases) to pass through the membranes.

sodium chloride (58 Da) is not retained by the 30 kDa membranes, whereas lactoferrin (80 kDa) is and for this reason lactoferrin eluting from the column at a low concentration (0.1% protein) can be concentrated to 3% protein, without a matching increase in the salt concentration or loss of protein.

UF5

Type: Spiral wound polyether sulphone (PES) MWCO: 5 kDa

Brand: Synder Model: MT2B-6338

The ultrafiltration plant known as UF5 was used to:
1. concentrate non-lactoferrin proteins eluted from the cation exchange column, and
2. recycle the 2.5% salt back to the 2.5% salt tank for reuse in the chromatographic process.

Justification of Process within the Broader Lactoferrin Manufacturing Process:

sodium chloride (2,000 kg per batch) is a significant cost ($1,200 per batch) in the lactoferrin manufacture process and the ability to recycle sodium chloride dramatically reduces the cost of production.

environmental damage is reduced by recycling sodium chloride. After tertiary treatment to remove organic solids, sodium chloride-containing effluent is disposed of by means of an ocean outfall and all steps must be taken to reduce the amount of waste generated. The salt recycling process reduces the amount of salt required by 80%, meaning that the amount of sodium chloride released into the environment is reduced by 8,000 kg per batch (one-third due to UF5).

Justification of Membrane Type:

spiral membranes are a comparatively cheap way of obtaining a large area of membrane, which allows high fluxes in a plant with a small foot print.

PES is an inherently hydrophilic membrane that wets out quickly and completely resulting in fast filtration with superior flow rates and high throughputs. PES membrane is also extremely low protein binding minimizing the likelihood of target protein binding, which means high yields, stable transmembrane fluxes and consistent apparent membrane porosities.

Justification of MWCO:

5 kDa membranes retain the non-lactoferrin impurities, which prevents them from returning to the chromatographic process and contaminating the lactoferrin during subsequent lactoferrin elutions. A smaller membrane is required because the proteins mixture contains many smaller proteins, many of which are growth factors.

sodium chloride (58 Da) is not retained by the 5 kDa membranes, whereas lactoperoxidase (80 kDa), immunoglobulins (150 to 420 kDa) and growth factors (5 to 17 kDa) are and for this reason proteins eluting from the column at a low concentration (0.1% protein) can be concentrated to 3% protein, without a matching increase in the salt concentration or loss of protein.

MF6

Type: Ceramic tubes (ALUMINA) MWCO: 0.8 μm

Brand: Pall Model: Membralox GP 19

The microfiltration plant known as MF6 was used to:
1. reduce the number of microbes present in the lactoferrin solution; and
2. remove insoluble material.

Justification of Membrane Type:

ceramic membranes have a high tolerance for cleaning chemicals and can be aggressively cleaned to ensure the complete removal of microbes. They are also very robust membranes that do not tear, which may allow contaminating material to pass through the membrane.

Justification of MWCO:

reduction in insoluble material (increased clarity) and microbial contamination the plant is 0.8 μm, rather than 0.22 μm, to allow the protein to be passed through the membrane at a reasonable volume and solids concentration. The filter is not intended to be a complete microbial removal step, since the main raw material (skimmed milk) has been previously pasteurised.

UF7

Type: Spiral wound polyvinylidene fluoride (PVDF) MWCO: 50 kDa

Brand: Synder Model: BN4B-6338

The ultrafiltration plant known as UF7 was used to:
1. increase the lactoferrin purity by reducing the non-lactoferrin proteins; and
2. increase the protein to >95% solids by removing sodium chloride and residual lactose.

Figure 14:
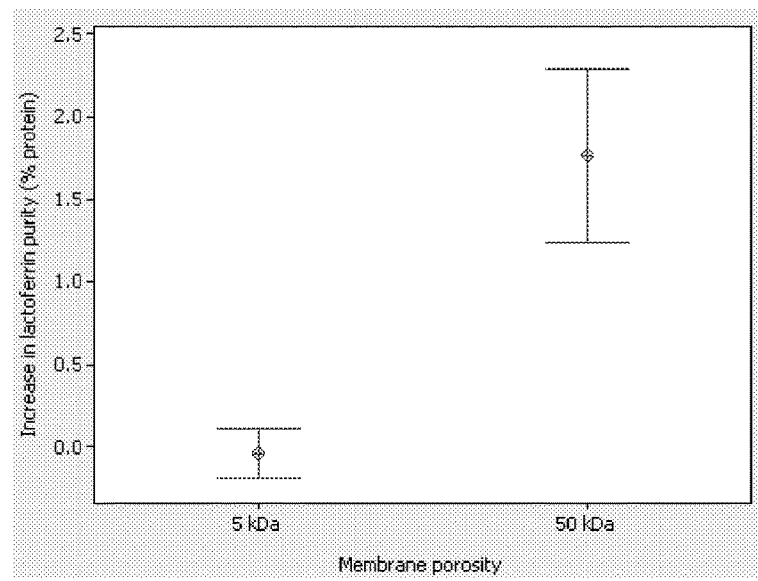
FIG. 14 illustrates the increase in lactoferrin purity due to processing through UF7 fitted with either the traditional 5 kDa membranes or the new 50 kDa membrane. Plotted values are means and bars indicate 95% confidence interval.

Justification of Process within the Broader Lactoferrin Manufacturing Process:

the lactoferrin intended for the manufacture of Ferritin OB has a higher lactoferrin purity than standard lactoferrin. The higher purity is obtained by substituting 50 kDa membranes for the 5 kDa membranes historically used (FIG. 14).

Justification of Membrane Type:

spiral membranes are a comparatively cheap way of obtaining a large area of membrane, which allows high fluxes and relatively short process times in a plant with a small foot print.

hydrophilic polyvinylidene fluoride (PVDF) membranes have high transmembrane fluxes and low affinity for proteins. For these reasons, fluxes remain high for the duration of the process and yields remain high because little protein fouls the membrane pours.

Justification of MWCO:
- 50 kDa membranes are used in preference to smaller membranes (historically 5 kDa membranes) because they allow improved transmission of non-lactoferrin proteins (RNases, growth factors), while retaining lactoferrin. The increased transmission of non-lactoferrin protein results in a higher lactoferrin purity (average increase in purity 1.8% protein, P<0.001). Further details can be obtained from 'Increasing Lactoferrin Purity by Diafiltration with Salt Solution in an Ultrafiltration Plant Fitted with 50 kDa Membranes' (JR0010).
- sodium chloride (58 Da) is not retained by the 50 kDa membranes, whereas lactoferrin (80 kDa) is and for this reason lactoferrin eluting from the column at a low concentration (3% protein) can be concentrated to >20% protein, without a matching increase in the salt concentration or loss of protein.
- increases total solids by removing water and therefore maximises freeze-dryer solids throughput.

Example 9: Fully Commercial Scale Trial to Confirm that the Purity of Lactoferrin can be Increased by 50 kDa UF To allow a comparison of the effectiveness of the change, a batch from the chromatographic process was split in half. Half was processed through UF7 fitted with 5 kDa membranes with no salt diafiltration and the other half was processed through UF7 fitted with 50 kDa membranes and salt diafiltration.

The routine commercial scale process was modified by replacing the 5 kDa membranes present in UF7 with Synder 50 kDa membranes identical to those used in experiments 1 and 6. A salt diafiltration step was also added to the commercial process. The salt used in the diafiltration solution was prepared by adding 150 kg sodium chloride to 3000 kg water.

The results presented in Table 1 show that the 50 kDa UF membranes and extra sodium chloride diafiltration step can increase the lactoferrin purity by 2.4% (protein basis). The final lactoferrin purity was 97.8% (protein basis) and approaches the target purity of 98.0% (protein basis). The composition of the protein was otherwise similar, suggesting that the process has no negative effects.

TABLE 1

A comparison of the composition lactoferrin made through the standard UF7 process and the high purity UF7 process, showing that the powders are similar, except for the increase in lactoferrin purity.

|  | Standard process LLL17FEB12B6 | High purity process LLL21FEB12B6 |
| --- | --- | --- |
| Moisture (% w/w) | 2.3 | 3.1 |
| Fat (% w/w) | 0.3 | 0.4 |
| Lactoferrin (% protein) | 95.4 | 97.8 |
| Ash (% w/w) | <0.1 | <0.1 |
| Protein (% w/w) | >97.3 | >96.4 |

In summary, the commercial scale trial produced a powder with a lactoferrin purity of 98.0% (protein basis), which was 1.1% higher in purity than the UF4 solution from which it was derived. The process was again shown to work successfully at a fully commercial scale. The diafiltration of lactoferrin solution with a salt solution in a UF plant fitted 50 kDa membranes has been shown to successfully increase the purity of lactoferrin by between 1% and 2.4% (protein basis) and can produce a product with a lactoferrin purity of 98% (protein basis). It appears that for the process to work at optimum level a sodium chloride concentration of 5% to 6% is required, which is convenient since 6% sodium chloride is used to elute the lactoferrin from the cation exchange column.

The invention claimed is:

1. A process for purifying lactoferrin from milk the process comprising subjecting the milk, to filtration with a filter of MWCO 30 kD to 50 kD to separate the milk into a retentate fraction comprising lactoferrin and a permeate fraction comprising growth factors and/or RNases, wherein during filtration with the filter of MWCO 30 kD to 50 kD the milk is subjected to salt treatment for at least 4 hours, such that growth factors and/or RNAses flow into the permeate, the salt treatment comprising maintaining the milk or retentate fraction at a salt concentration of at least 0.2M NaCl or equivalent or a conductivity of at least 20 mS/cm during filtration with the filter of MWCO 30 kD to 50 kD.

2. The process of claim 1 in which the filter has a MWCO of 50 kD.

3. The process of claim 1 in which the filtration is carried out at 50-70 degrees centigrade.

* * * * *